Figure 1:
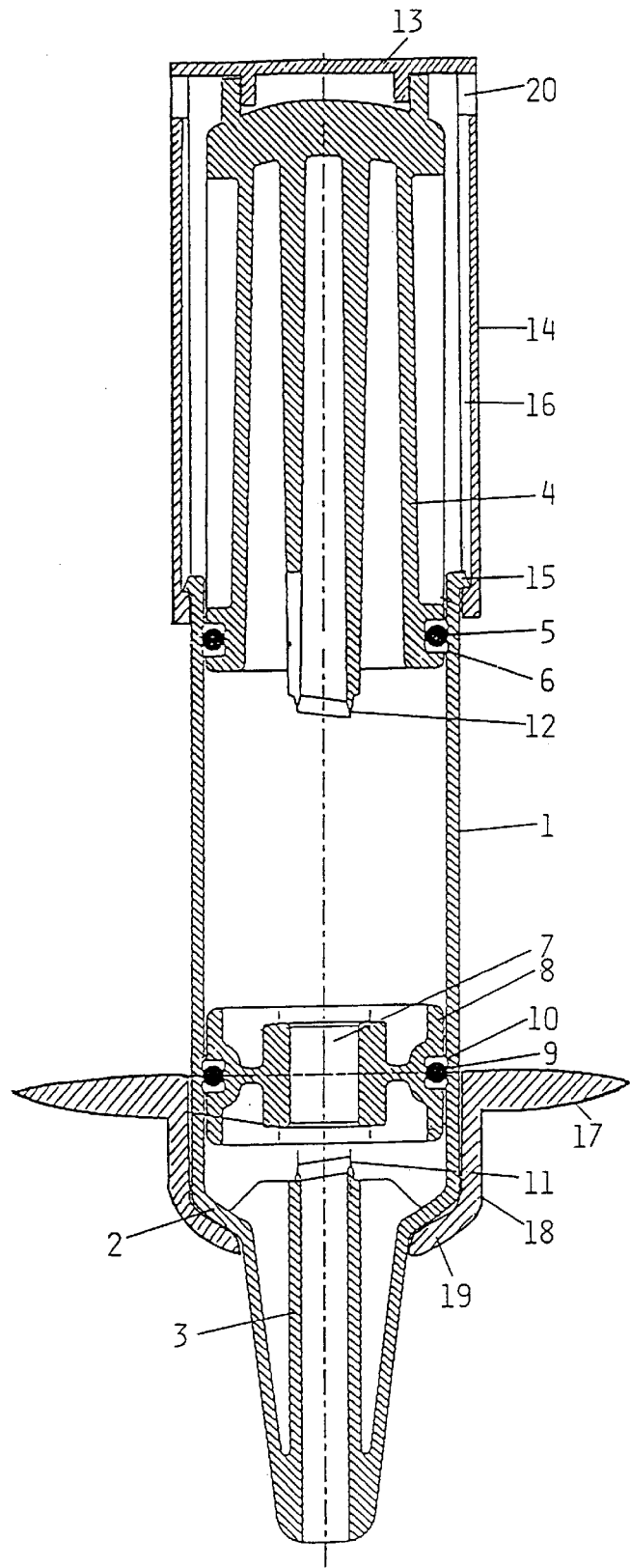

United States Patent

Petersen et al.

[11] Patent Number: 6,156,014
[45] Date of Patent: *Dec. 5, 2000

[54] DISPENSER SECURED AGAINST REUSE

[75] Inventors: Kim Stengaard Petersen, Hvidovre; Svend Elk, Birkeroed; Hans Köster, Hellerup, all of Denmark

[73] Assignee: Novo Nordisk A/S, Bagsværd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 09/428,761

[22] Filed: Oct. 28, 1999

Related U.S. Application Data

[63] Continuation of application No. 08/530,312, filed as application No. PCT/DK94/00125, Mar. 25, 1994, Pat. No. 5,984,897.

[30] Foreign Application Priority Data

Apr. 1, 1993 [DK] Denmark ................................. 0392/93

[51] Int. Cl.[7] ...................................................... A61M 5/00
[52] U.S. Cl. ............................................ 604/218; 604/187
[58] Field of Search ..................................... 604/218, 187, 604/208, 220, 228, 229, 222

[56] References Cited

U.S. PATENT DOCUMENTS

| 3,943,927 | 3/1976 | Norgren | 604/218 |
| 4,091,812 | 5/1978 | Helixon | 604/218 X |
| 5,984,897 | 11/1999 | Petersen et al. | 604/187 |

FOREIGN PATENT DOCUMENTS

| 27 14 818 | 10/1977 | Germany . |
| WO91/11212 | 8/1991 | WIPO . |
| WO92/06727 | 4/1992 | WIPO . |

*Primary Examiner*—John D. Yasko
*Attorney, Agent, or Firm*—Steve T. Zelson, Esq.

[57] ABSTRACT

A dispenser for dispersing of a drug comprising a housing (1) forming a cylinder. The cylinder is at one end closed by an end wall (2) having an outlet pipe (3) and the other end is closed by a plunger (4) which is axially displaceable into the cylinder. The outer end of the plunger (4) is secured to the inner side of a cup shaped cap (13, 14) sliding over the outer side of the cylinder. When the plunger (4) is pressed into the cylinder, the upper edge of the housing (1) being provided with outwardly projecting hooks (15) sliding in corresponding grooves (16) in the inner side of the side wall (14) of the cap wall irreversibly engage windows (20) at the bottom (13) of the cap. The cap (13, 14) and the housing (1) is made from differently colored materials.

4 Claims, 1 Drawing Sheet

DISPENSER SECURED AGAINST REUSE

CROSS-REFERENCE TO RELATED APPLICATIONS

This application is a continuation of U.S. application Ser. No. 08/530,312 filed Sep. 13, 1995 now U.S. Pat. No. 5,984,897, which is a 35 U.S.C. 371 national application of PCT/DK94/00125 filed Mar. 25, 1994, which claims priority under 35 U.S.C. 119 of Danish application 0392/93 filed Apr. 1, 1993, the contents of which are fully incorporated herein by reference.

The invention relates to dispensers for dispensing a dosage of a drug, this dispenser comprising a housing forming a cylinder which is at one end closed by an end wall provided with an outlet pipe, and at the other end closed by a plunger projecting from this open end of the cylinder and being axially displaceable into the cylinder towards the end wall.

Such dispensers are described in EP 407 276 and Danish patent application No. 1985/91. Whereas these publications describe excellent solutions of the dispensing problem, they do not deal with the security demands which must be made on such dispensers. These demands are:
1. No removal of the plunger from the cylinder is allowed.
2. The plunger is not allowed to be pulled outwards when once pressed home in the cylinder.
3. The appearance of the dispenser clearly indicates whether the dispenser is used or unused.
4. An auditive indication when the dosage is expelled.

These demands may be fulfilled by a dispenser of the kind described in the introduction of this specification, which dispenser is characterized in that the outer end of the plunger is secured to the inner side of the bottom of a cup shaped cap which slides over the outer side of the cylinder when the plunger is pressed into this cylinder, the upper edge of the cylinder being provided with outwardly projecting hooks sliding in corresponding grooves in the inner surface of the side wall of the cap, these grooves ending at a distance from the edge of the open end of the cup, and openings being provided through the side wall of the cap at the ends of the grooves at the bottom of the cap.

A dispenser designed along these lines will fulfil the demands, as when engaging the grooves in the inner surface of the side wall of the cap, the hooks will abut the edge formed where the grooves end near the open end of the cap, and this will prevent the cap from being pulled off the cylinder once it has been mounted. When the piston is pressed home in the cylinder, the cap will slide over this cylinder, and the hooks will reach the openings through the wall of the cap near the bottom of this cap at the ends of the grooves, and the hooks will snap into these openings and thereby prevent the cap and consequently the plunger from being drawn back once it has been pressed home in the cylinder. The appearance of the device changes conspicuously when the device is used, as after use the cap hides the outer surface of the cylinder, and the hooks become visible in the openings at the bottom of the cap. Further, the hooks snapping into the openings will give an auditive indication of the fact that the plunger has been pressed home and the dosage is expelled.

Appropriately, a finger grip may be provided secured to the closed end of the cylinder, this finger grip comprising an annular part fitting over the closed end of the cylinder and having an inward flange abutting the end wall of this cylinder. When the cap is intended to slide over the cylinder, finger grips cannot be provided at the open end of the cylinder as they are in the known syringes. By the provision of the finger grips at the lower end of the cylinder as a separately moulded part secured to the cylinder, mouldings on the outer side of the barrel providing a local increase of the thickness of the wall are avoided. Local increases of the thickness of the wall could provoke unwanted sink marks on the inner surface of the cylinder during the hardening of the moulding material.

When the finger grip and the cap, the plunger, and the cylinder are made of differently coloured materials, the changes of the appearance of the device when changing from non-used to used condition become more conspicuous. The closed end of the cylinder being covered by the finger grip leaves the colour of the cylinder visible as long as the cylinder is not covered by the cap, i.e. in the non-used condition. In this condition also the colour of the plunger is visible through the openings at the bottom of the cap. When the device is used, and the cap covers the cylinder, the device will appear with the colour of the cap and the colour of the finger grip, and the colour seen in the openings will change from the colour of the plunger to the colour of the cylinder, as the hooks at the edge of the cylinder will appear in the openings, and the colour of the plunger will be hidden behind the hooks.

To make sure that the plunger remains in its outermost position until the device is taken into use, the plunger may at its inner end be provided by an O-ring cooperating sealingly with the inner surface of the cylinder, and an annular recess may be provided in this surface near the open end of the cylinder to be engaged by the O-ring when the plunger is in its outermost position.

In the following the invention will be further described with references to the drawing schematically showing a sectional view of a dispenser according to the invention.

The dispenser shown in the drawing is of the known kind comprising a cylinder body 1 closed at one end by an end wall 2, through which an outlet pipe communicates with the interior of the cylinder. At its other end the cylinder is closed by a plunger 4 having at its distal end a circumferential recess accommodating an O-ring 5 cooperating sealingly with the inner surface of the cylinder body 1. Near the open end of the cylinder this surface is provided with a shallow circumferential recess 6, in which the O-ring is lodged until the device is taken into use. Thereby the plunger is secured against being inadvertently pushed into the cylinder, as some pressure must be added to the plunger to make the O-ring get out of the recess 6.

The drug which should be dispensed by the device is stored in a chamber 7 in a piston 8, which is maintained in position in the cylinder by having an O-ring 9 in a circumferential recess in the piston cooperating sealingly with the inner surface of the cylinder, in which surface the O-ring 9 engages a circumferential recess 10, until a pressure sufficient to move the piston 8 forward is built up behind this piston by pressing the plunger 4 into the cylinder. When the piston is moved forward towards the end wall of the cylinder, a penetrator 11 at the inner end of the outlet tube 3 penetrates a membrane sealing one end of the chamber 7. When the plunger 4 is pressed home into the cylinder, a second penetrator 12 carried by the plunger 4 will penetrate another membrane sealing the other end of the chamber 7, and the air compressed by the plunger in the cylinder will escape through the outlet pipe 3 entraining the drug in the chamber 7.

The proximal end of the plunger 4 is by a not shown snap lock or a similar securing device secured to the bottom 13 of a cup shaped cap having a wall 14 which slides along the outer surface of the cylinder body 1, when the plunger 7 is pressed into the cylinder. Hooks 15 projecting outwards at the open end of the cylinder engage longitudinal internal grooves 16 in the wall 14. These grooves 16 end at a distance from the edge of the cap, thereby providing an abutment for the hooks 15, so that the cap may not immediately be pulled free of the cylinder body 1 once mounted thereon. When the plunger is pressed into the cylinder, the hooks 15 will slide along the grooves 16, until they reach the bottom of the cap. Here windows 20 are made through the wall 14, and due to their resilience the hooks 15 will irreversibly snap into these windows 20 and block the plunger against withdrawal.

A pair of finger grips 17 are carried by a ring 18, which is fitted on the distal end of the cylinder body 1, this ring having an inward flange 19 abutting the end wall 2 of the cylinder to limit the movement of the ring along the cylinder body 1. In the position where the flanges 19 engage the end wall 2, the ring is secured to the cylinder body by a not shown snap lock.

The cylinder may have a conspicuous colour, e.g. red or orange, whereas the cap, the finger grips 17, the ring 18, and the flange may e.g. be grey. When the device is non-used, it will appear with a broad conspicuously coloured band due to the main part of the cylinder body 1 being visible. Further, the piston which may be glimpsed through the windows 20 may have a colour commonly interpreted as a ready for use signal, e.g. green.

As long as the device is non-used the green colour is seen in the windows 20. When the piston is pressed home, the hooks 15 snap into the windows, and being made integral with the cylinder body 1 these hooks will appear as red or orange indications in the windows 20. Further, the conspicuous band around the device will disappear, as the cylinder body 1 is covered by the grey cap wall 14.

What is claimed is:

1. A dispenser for dispensing a dosage of a drug, this dispenser comprising a housing forming a cylinder which is at one end closed by an end wall provided with an outlet pipe, and at the other end closed by a plunger projecting from this open end of the cylinder and being axially displaceable into the cylinder towards the end wall, characterized in, that the outer end of the plunger is secured to the inner side of the bottom of a cup shaped cap which slides over the outer side of the cylinder, when the plunger is pressed into this cylinder, the upper edge of the cylinder being provided with outwardly projecting hooks sliding in corresponding grooves in the inner surface of the side wall of the cap, these grooves ending at a distance from the edge of the open end of the cup, and openings being provided through the side wall of the cap at the end of the grooves at the bottom of the cap.

2. A dispenser according to claim 1, characterized in, that a finger grip is provided secured to the closed end of the cylinder, this finger grip comprising an annular part fitting over the closed end of the cylinder, and having an inward flange abutting the end wall of this cylinder.

3. A dispenser according to claim 2, characterized in, that the cylinder, the plunger, and the cap and finger grip are made of differently coloured materials.

4. A dispenser according to claim 1, characterized in, that the plunger at its inner end is provided by an O-ring cooperating sealingly with the inner surface of the cylinder, and that an annular recess is provided in this surface near the open end of the cylinder to be engaged by the O-ring, when the plunger is in its outermost position.

* * * * *